(12) United States Patent
Maeda et al.

(10) Patent No.: US 9,179,859 B2
(45) Date of Patent: Nov. 10, 2015

(54) COMPARTMENTAL ANALSYS SYSTEM, COMPARTMENTAL ANALYSIS METHOD, COMPARTMENT ANALYZER, PROGRAM, AND RECORDING MEDIUM

(71) Applicant: TAIYO NIPPON SANSO CORPORATION, Tokyo (JP)

(72) Inventors: Akihiko Maeda, Zushi (JP); Takashi Kambe, Tsuchiura (JP); Takeshi Ochi, Kawasaki (JP)

(73) Assignee: TAIYO NIPPON SANSO CORPORATION, Tokyo (JP)

( * ) Notice: Subject to any disclaimer, the term of this patent is extended or adjusted under 35 U.S.C. 154(b) by 307 days.

(21) Appl. No.: 13/705,258

(22) Filed: Dec. 5, 2012

(65) Prior Publication Data

US 2013/0150706 A1    Jun. 13, 2013

(30) Foreign Application Priority Data

Dec. 8, 2011    (JP) ................. 2011-269143

(51) Int. Cl.
*A61B 5/05* (2006.01)
*A61B 5/055* (2006.01)
(Continued)

(52) U.S. Cl.
CPC ............... *A61B 5/055* (2013.01); *A61B 5/0042* (2013.01); *A61B 5/0263* (2013.01); *A61B 5/0275* (2013.01); *A61B 5/4064* (2013.01); *A61B 5/489* (2013.01); *A61B 5/7225* (2013.01)

(58) Field of Classification Search
CPC .......... G06F 17/10; G06G 7/60; A61B 5/055; A61M 6/00; A62B 7/00
See application file for complete search history.

(56) References Cited

U.S. PATENT DOCUMENTS 8,554,305 B2 * 10/2013 Tailor et al. ................... 600/420
2002/0042569 A1    4/2002 Wedeen
(Continued)

FOREIGN PATENT DOCUMENTS

JP    2002-267756    9/2002
JP    2008-239566    10/2008

OTHER PUBLICATIONS

Michio Senda, "The $20^{th}$ influx and distribution volume", *Nuclear Medicine Document Information—Seminar*[online], Dec. 2009, accessed on Oct. 6, 2011, URL:http://www.asca-co.com/nuclear/2009/12/post-22.html, 5 pages—w/ Full Translation.
(Continued)

*Primary Examiner* — Unsu Jung
*Assistant Examiner* — Joel Lamprecht
(74) *Attorney, Agent, or Firm* — Nixon & Vanderhye P.C.

(57) ABSTRACT

One object of the present invention is to perform compartmental analysis of the dynamics of a tracer in the brain, and the present invention provides a compartmental analysis system including a measurement apparatus that measures the strength of an electromagnetic wave from a tracer and a compartmental analyzer that performs compartmental analysis of the dynamics of the tracer in the brain on the basis of the strength of the electromagnetic wave, wherein the compartmental analyzer includes a rate constant calculation unit that calculates a rate constant when the tracer moves between compartments on the basis of the strength of an electromagnetic wave in a first compartment corresponding to the cerebral blood vessel in the brain or an input function in the first compartment, the strength of an electromagnetic wave in a second compartment corresponding to the brain tissue in the brain, and the strength of an electromagnetic wave in a third compartment corresponding to the cerebral sulcus or cerebral ventricle in the brain.

18 Claims, 5 Drawing Sheets

(51) Int. Cl.
*A61B 5/00* (2006.01)
*A61B 5/026* (2006.01)
*A61B 5/0275* (2006.01)

(56) References Cited

U.S. PATENT DOCUMENTS

2003/0211036 A1 11/2003 Degani et al.
2004/0030240 A1 2/2004 Kimura
2011/0035198 A1 2/2011 McGrath et al.

OTHER PUBLICATIONS

Michio Senda, "The 24th imaging of cerebral blood flow and metabolism", *Nuclear Medicine Document Information Seminar* [online], Apr. 2010, accessed on Oct. 6, 2011, URL:http//www.asca-co.com/nuclear/2010/04/post-26.html, 3 pages—w/ Partial Translation.
Extended Search Report issued EP Appl 12194423.5 on Apr. 3, 2013.
May 19, 2015 Office Action issued in Japanese Patent Application No. 2011-269143 (with English-language translation).

* cited by examiner

FIG. 3

| VOXEL ID | COORDINATES | | | | COMPARTMENT | STRENGTH |
|---|---|---|---|---|---|---|
| V0001 | (X1a, Y1a, Z1a), | (X1b, Y1b, Z1b), | (X1c, Y1c, Z1c), | ... | 2 | Br1 (t) |
| V0002 | (X2a, Y2a, Z2a), | (X2b, Y2b, Z2b), | (X2c, Y2c, Z2c), | ... | 3 | C2 (t) |
| V0003 | (X3a, Y3a, Z3a), | (X3b, Y3b, Z3b), | (X3c, Y3c, Z3c), | ... | 1 | Bl3 (t) |
| ...... | ...... | | | | ...... | ...... |

119

COMPARTMENTAL ANALSYS SYSTEM, COMPARTMENTAL ANALYSIS METHOD, COMPARTMENT ANALYZER, PROGRAM, AND RECORDING MEDIUM

This application claims priority to JP Patent Application No. 2011-269143 filed Dec. 8, 2011, the entire content which is hereby incorporated by reference.

BACKGROUND OF THE INVENTION

1. Field of the Invention

The present invention relates to a compartmental analysis system, a compartmental analysis method, a compartmental analyzer, a program, and a recording medium. In particular, the present invention relates to a compartmental analysis system that performs compartmental analysis of the dynamics of a tracer in the brain, a compartmental analysis method and a compartmental analyzer that perform compartmental analysis of the dynamics of a tracer in the brain on the basis of the strength of an electromagnetic wave from a tracer in the brain measured by a measurement apparatus, a program causing a computer to function as the compartmental analyzer, and a recording medium on which the program is recorded.

2. Description of Related Art

Diseases, such as cerebrovascular disorder or dementia, may be evaluated using cerebral blood flow as an index. As a method of analyzing the cerebral blood flow, a method of performing compartmental analysis of the dynamics of cerebral blood flow exuded from cerebral blood vessels is known (for example, refer to Michio Senda, "The 20th influx and distribution volume", [online], December 2009, nuclear medicine document information seminar, [accessed on Oct. 6, 2011], the Internet, <URL:http://www.asca-co.com/nuclear/2009/12/post-22.html> and Michio Senda, "The 24th imaging of cerebral blood flow and metabolism", [online], April 2010, nuclear medicine document information seminar, [accessed on Oct. 6, 2011], the Internet, <URL:http://www.asca-co.com/nuclear/2010/04/post-26.html>). More specifically, the dynamics of cerebral blood flow is measured by positron emission tomography using a radioactive chemical as a tracer, for example. In addition, the dynamics of cerebral blood flow is analyzed by a two-compartment model formed by two compartments of cerebral blood vessels and brain tissue. In the analysis using the two-compartment model, it is assumed that all arterial blood arriving at a section of the brain moves to the brain tissue.

In the method of analyzing the dynamics of cerebral blood flow using the two-compartment model, a detailed anatomical stereoscopic image of the patient's brain, that is, a morphological image, is generally captured by an X-ray CT (Computed Tomography) apparatus. In addition, each region of the cerebral blood vessels and brain tissue in which the dynamics of cerebral blood flow needs to be analyzed is determined with reference to the image captured by the X-ray CT apparatus. Then, a functional image of the brain is captured by injecting a radioactive chemical as a tracer into the patient. Then, a temporal change in the amount of radiation in each region of the cerebral blood vessels and brain tissue is measured. In addition, a rate constant K1 when the tracer moves from the cerebral blood vessel to the brain tissue and a rate constant K2 when the tracer moves from the brain tissue to the cerebral blood vessel are calculated on the basis of the measured amount of radiation. In addition, the calculated rate constants K1 and K2 are used to calculate the cerebral blood flow (which means the amount of radioactive tracer that flows from the blood vessel and reaches the brain cell tissue).

The rate constants K1 and K2 calculated by the analysis using the two-compartment model are useful parameters to analyze the dynamics of cerebral blood flow in the brain. Here, the dynamics of cerebral blood flow in the brain is associated with the dynamics of cerebrospinal fluid in the cerebral sulcus or cerebral ventricle. However, the analysis using the two-compartment model described above focuses on only the dynamics of a tracer between cerebral blood vessels and brain tissue. Therefore, it is difficult for very useful parameters to analyze the dynamics of cerebral blood flow in the brain to be calculated.

SUMMARY OF THE INVENTION

In order to solve the above-described problems, according to a first aspect of the invention, a compartmental analysis system that performs compartmental analysis of dynamics of a tracer in a brain includes: a measurement apparatus that measures a strength of an electromagnetic wave from the tracer in the brain; and a compartmental analyzer that performs compartmental analysis of dynamics of the tracer in the brain on the basis of the strength of the electromagnetic wave from the tracer in the brain measured by the measurement apparatus, wherein the compartmental analyzer includes a rate constant calculation unit that calculates a rate constant when the tracer moves between the compartments on the basis of a strength of an electromagnetic wave in a first compartment corresponding to a cerebral blood vessel in the brain measured by the measurement apparatus or an input function in the first compartment, a strength of an electromagnetic wave in a second compartment corresponding to brain tissue in the brain measured by the measurement apparatus, and a strength of an electromagnetic wave in a third compartment corresponding to a cerebral sulcus or a cerebral ventricle in the brain measured by the measurement apparatus.

The compartmental analyzer may further include a compartment-specifying unit that specifies to which one of the compartments a part of the brain in each of a plurality of divided regions obtained by dividing the brain corresponds. The rate constant calculation unit may calculate the rate constant when the tracer moves between the compartments on the basis of a strength of an electromagnetic wave in a divided region specified to correspond to the first compartment by the compartment-specifying unit, a strength of an electromagnetic wave in a divided region specified to correspond to the second compartment by the compartment-specifying unit, and a strength of an electromagnetic wave in a divided region specified to correspond to the third compartment by the compartment-specifying unit.

The compartmental analyzer may further include a region division unit that divides the brain into a plurality of divided regions, and the compartment-specifying unit may specify to which one of the compartments a part of the brain in each of the plurality of divided regions divided by the region division unit corresponds.

The compartmental analyzer may further include an instruction-receiving unit that receives an instruction to specify a region-of-interest of the brain, which is to be subjected to compartmental analysis, and the region division unit may divide the region-of-interest, which is specified by the instruction received by the instruction-receiving unit, into a plurality of divided regions.

The tracer may be $H_2^{17}O$.

The measurement apparatus may be an MRI apparatus.

According to a second aspect of the invention, a compartmental analysis method of performing compartmental analysis of dynamics of a tracer in a brain on the basis of a strength of an electromagnetic wave from the tracer in the brain measured by a measurement apparatus includes: a step of calculating a rate constant when the tracer moves between the compartments on the basis of a strength of an electromagnetic wave in a first compartment corresponding to a cerebral blood vessel in the brain measured by the measurement apparatus or an input function in the first compartment, a strength of an electromagnetic wave in a second compartment corresponding to brain tissue in the brain measured by the measurement apparatus, and a strength of an electromagnetic wave in a third compartment corresponding to a cerebral sulcus or a cerebral ventricle in the brain measured by the measurement apparatus.

According to a third aspect of the invention, a compartmental analyzer that performs compartmental analysis of dynamics of a tracer in a brain on the basis of a strength of an electromagnetic wave from the tracer in the brain measured by a measurement apparatus includes: a rate constant calculation unit that calculates a rate constant when the tracer moves between the compartments on the basis of a strength of an electromagnetic wave in a first compartment corresponding to a cerebral blood vessel in the brain measured by the measurement apparatus or an input function in the first compartment, a strength of an electromagnetic wave in a second compartment corresponding to brain tissue in the brain measured by the measurement apparatus, and a strength of an electromagnetic wave in a third compartment corresponding to a cerebral sulcus or a cerebral ventricle in the brain measured by the measurement apparatus.

According to a fourth aspect of the invention, a program is provided causing a computer to function as a compartmental analyzer that performs compartmental analysis of dynamics of a tracer in a brain on the basis of a strength of an electromagnetic wave from the tracer in the brain measured by a measurement apparatus, and the program causes the computer to function as a rate constant calculation unit that calculates a rate constant when the tracer moves between the compartments on the basis of a strength of an electromagnetic wave in a first compartment corresponding to a cerebral blood vessel in the brain measured by the measurement apparatus or an input function in the first compartment, a strength of an electromagnetic wave in a second compartment corresponding to brain tissue in the brain measured by the measurement apparatus, and a strength of an electromagnetic wave in a third compartment corresponding to a cerebral sulcus or a cerebral ventricle in the brain measured by the measurement apparatus.

According to a fifth aspect of the invention, a recording medium recording a program is provided causing a computer to function as a compartmental analyzer that performs compartmental analysis of dynamics of a tracer in a brain on the basis of a strength of an electromagnetic wave from the tracer in the brain measured by a measurement apparatus, and the recording medium recording a program causes the computer to function as a rate constant calculation unit that calculates a rate constant when the tracer moves between the compartments on the basis of a strength of an electromagnetic wave in a first compartment corresponding to a cerebral blood vessel in the brain measured by the measurement apparatus or an input function in the first compartment, a strength of an electromagnetic wave in a second compartment corresponding to brain tissue in the brain measured by the measurement apparatus, and a strength of an electromagnetic wave in a third compartment corresponding to a cerebral sulcus or a cerebral ventricle in the brain measured by the measurement apparatus.

In addition, the summary of the invention described above is not intended to list all necessary features of the invention.

In addition, sub-combinations of these features may also be regarded as the invention.

As is apparent from the above explanation, according to the invention, parameters more useful than parameters that can be obtained by the analysis using a two-compartment model can be calculated as parameters for analyzing the dynamics of cerebral blood flow in the brain.

BRIEF DESCRIPTION OF THE DRAWINGS

FIG. 3 is a view showing an example of the information, which is stored in a region-of-interest information storage unit 119, in a table form.

DETAILED DESCRIPTION OF THE INVENTION

Hereinafter, the invention will be described through embodiments of the invention. However, the following embodiments do not limit the invention defined in the appended claims, and all combinations of the features described in the embodiments are not always necessary for the solving means of the invention.

Figure 1:
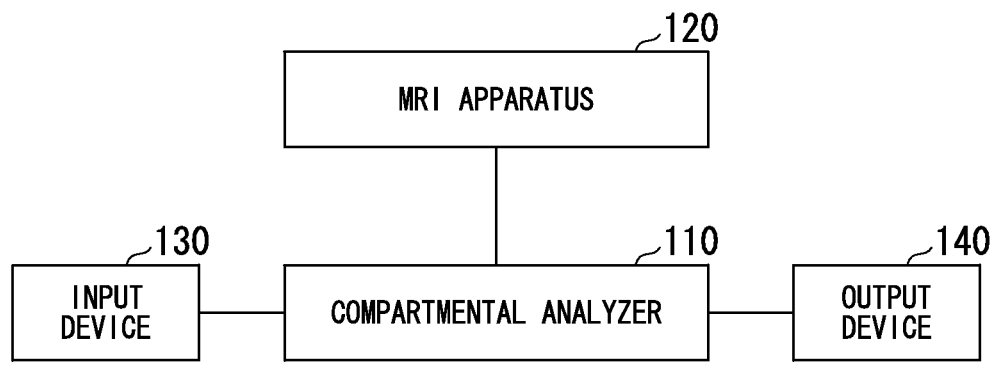
FIG. 1 is a view showing an example of the environment of the use of a compartmental analysis system 100 according to an embodiment.

FIG. 1 shows an example of the environment of the use of a compartmental analysis system 100 according to an embodiment. The compartmental analysis system 100 is a system that performs compartmental analysis of dynamics of $H_2^{17}O$ in the brain. Here, $H_2^{17}O$ contains many water molecules with isotopes with large mass numbers, and is water with a larger specific gravity than normal water. In addition, $H_2^{17}O$ may be an example of "tracer" in this invention.

The compartmental analysis system 100 includes a compartmental analyzer 110, an MRI (Magnetic Resonance Imaging) apparatus 120, an input device 130, and an output device 140. The compartmental analyzer 110 is electrically connected to each of the MRI apparatus 120, the input device 130, and the output device 140. In addition, the MRI apparatus 120 may be an example of a "measurement apparatus" in this invention.

The compartmental analyzer 110 is an apparatus that performs compartmental analysis of the dynamics of $H_2^{17}O$ in the brain on the basis of the strength of a nuclear magnetic resonance signal from $H_2^{17}O$ in the brain measured by the MRI apparatus 120. In addition, the nuclear magnetic resonance signal may be an example of an "electromagnetic wave" in this invention.

The MRI apparatus 120 is an apparatus that recreates the information inside the body as a three-dimensional image using a nuclear magnetic resonance phenomenon. More specifically, the MRI apparatus 120 measures the strength of a nuclear magnetic resonance signal in the brain.

The input device 130 is a device that inputs data, information, instructions, and the like to the compartmental analyzer 110.

The output device 140 is a device that receives data or information from the compartmental analyzer 110 and presents it in a form that can be recognized by a human being.

Figure 2:
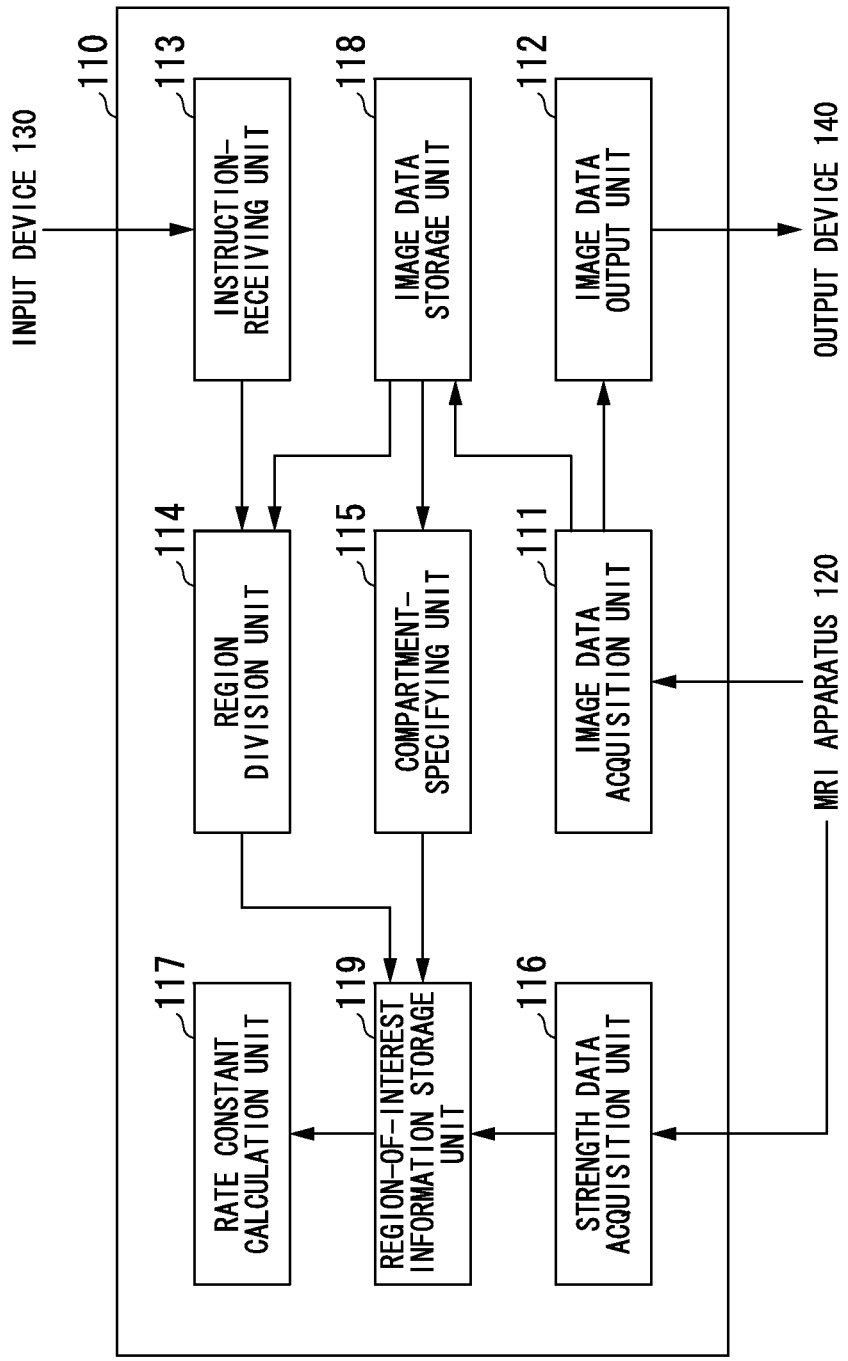
FIG. 2 is a view showing an example of the block configuration of a compartmental analyzer 110.

FIG. 2 shows an example of the block configuration of the compartmental analyzer 110. The compartmental analyzer 110 includes an image data acquisition unit 111, an image data output unit 112, an instruction-receiving unit 113, a region division unit 114, a compartment-specifying unit 115, a strength data acquisition unit 116, a rate constant calculation unit 117, an image data storage unit 118, and a region-of-interest information storage unit 119. Hereinafter, a function and an operation of each component will be described.

The image data acquisition unit 111 acquires three-dimensional image data of the photographed brain from the MRI apparatus 120.

The image data output unit 112 outputs the three-dimensional image data of the photographed brain to the output device 140.

The instruction-receiving unit 113 receives an instruction to specify a region-of-interest of the brain, which is to be subjected to compartmental analysis, through the input device 130.

The region division unit 114 divides the brain into a plurality of voxels. More specifically, the region division unit 114 divides the region-of-interest, which is specified by the instruction received by the instruction-receiving unit 113, into a plurality of voxels. Here, the voxel is a volume element, and indicates a value of a rectangular parallelepiped unit in three-dimensional space. For example, when a cube of 10 cm (vertical)×10 cm (horizontal)×5 cm (height) is a region-of-interest, the "vertical×horizontal" plane can be divided into a matrix. Here, each lattice plane obtained by division into a matrix is called a pixel. In this case, a voxel is obtained by multiplying a pixel by the height. In addition, the voxel may be an example of a "divided region" in this invention.

The compartment-specifying unit 115 specifies to which one of a first compartment corresponding to a cerebral blood vessel, a second compartment corresponding to brain tissue, and a third compartment corresponding to a cerebral sulcus or cerebral ventricle a part of the brain in each of a plurality of voxels obtained by dividing the brain corresponds. More specifically, the compartment-specifying unit 115 specifies to which one of the compartments a part of the brain in each of a plurality of voxels divided by the region division unit 114 corresponds.

The strength data acquisition unit 116 acquires data, which indicates the strength of the nuclear magnetic resonance signal for each voxel in the brain, from the MRI apparatus 120.

The rate constant calculation unit 117 calculates the rate constant when $H_2{}^{17}O$ moves between the compartments on the basis of the strength of the nuclear magnetic resonance signal in the first compartment in the brain measured by the MRI apparatus 120, the strength of the nuclear magnetic resonance signal in the second compartment in the brain measured by the MRI apparatus 120, and the strength of the nuclear magnetic resonance signal in the third compartment in the brain measured by the MRI apparatus 120. More specifically, the rate constant calculation unit 117 calculates the rate constant when $H_2{}^{17}O$ moves between the compartments on the basis of the strength of a nuclear magnetic resonance signal in a voxel specified to correspond to the first compartment by the compartment-specifying unit 115, the strength of a nuclear magnetic resonance signal in a voxel specified to correspond to the second compartment by the compartment-specifying unit 115, and the strength of a nuclear magnetic resonance signal in a voxel specified to correspond to the third compartment by the compartment-specifying unit 115.

FIG. 3 shows an example of information stored in the region-of-interest information storage unit 119 in a table format. In the region-of-interest information storage unit 119, information of voxel ID, coordinates, compartments, and the strength are stored so as to match with each other.

The voxel ID information is an identification code for uniquely identifying each voxel in a plurality of voxels. The coordinate information is information for specifying the position of the voxel identified by the voxel ID. The compartment information is information indicating a compartment to which a part of the brain in the voxel identified by the voxel ID corresponds. The strength information is information indicating the strength of the nuclear magnetic resonance signal in the voxel identified by the voxel ID.

Figure 4:
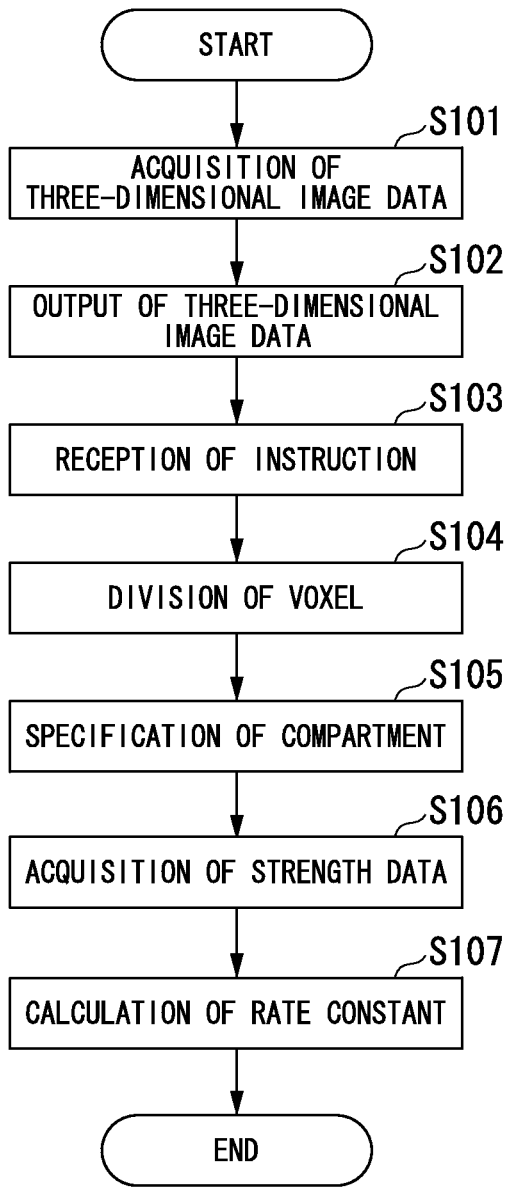
FIG. 4 is a view showing an example of the operation flow of the compartmental analyzer 110.

FIG. 4 shows an example of the operation flow of the compartmental analyzer 110. FIGS. 1 to 3 will be referred to in explanation of this operation flow.

A doctor photographs the inside of the brain of a patient using the MRI apparatus 120 before injecting $H_2{}^{17}O$ into the patient. The MRI apparatus 120 recreates the information in the brain as three-dimensional image data using a nuclear magnetic resonance phenomenon and outputs it to the compartmental analyzer 110.

When the three-dimensional image data obtained by photographing the inside of the brain is acquired from the MRI apparatus 120 (S101), the image data acquisition unit 111 of the compartmental analyzer 110 transmits the three-dimensional image data to the image data output unit 112 and also stores the three-dimensional image data in the image data storage unit 118.

When the three-dimensional image data transmitted from the image data acquisition unit 111 is received, the image data output unit 112 of the compartmental analyzer 110 outputs the three-dimensional image data to the output device 140 (S102). In this manner, the output device 140 outputs a three-dimensional image obtained by photographing the inside of the brain.

A doctor determines a region-of-interest of the brain, which is to be subjected to compartmental analysis, in the three-dimensional image of the brain output from the output device 140. For example, when a patient has an ischemic problem, a doctor determines the ischemic part as a region-of-interest. Then, the doctor gives an instruction to specify the determined region-of-interest using the input device 130.

When the instruction to specify a region-of-interest of the brain to be subjected to compartmental analysis is received through the input device 130 (S103), the instruction-receiving unit 113 of the compartmental analyzer 110 transmits data indicating the specified region-of-interest of the brain to the region division unit 114. For example, the instruction-receiving unit 113 transmits data indicating a plurality of coordinates in a three-dimensional image, which indicate the outer edge of the specified region-of-interest of the brain, to the region division unit 114 as data indicating the region-of-interest of the brain.

When the data transmitted from the instruction-receiving unit 113 is received, the region division unit 114 of the compartmental analyzer 110 divides the region-of-interest, which is indicated by the data received from the instruction-receiving unit 113, into a plurality of voxels with reference to the three-dimensional image data stored in the image data storage unit 118 (S104). For example, the region division unit 114 divides the region-of-interest into tens to hundreds of voxels or more. In addition, the region division unit 114 stores the information of the coordinates for specifying the position of each voxel in the region-of-interest information storage unit 119 so as to match the information of the voxel ID for identifying each voxel. Here, the coordinate information may be coordinates of eight apices of a voxel, for example.

When the voxel position information is stored in the region-of-interest information storage unit 119, the compartment-specifying unit 115 of the compartmental analyzer 110 specifies, with reference to the three-dimensional image data stored in the image data storage unit 118, to which one of the first compartment corresponding to the cerebral blood vessel, the second compartment corresponding to brain tissue, and the third compartment corresponding to the cerebral sulcus or cerebral ventricle a part of the brain in each of the plurality of voxels obtained by dividing the brain corresponds (S105). Here, the environment of water present in each part of the cerebral blood vessel, brain tissue, cerebral sulcus, and cerebral ventricle is different. The relaxation time of H is also different in each of these parts. The MRI apparatus 120 generates a three-dimensional image of the brain on the basis of such information. Accordingly, the compartment-specifying unit 115 can specify to which part of the cerebral blood vessel, brain tissue, cerebral sulcus, and cerebral ventricle the part of the brain reflected in each voxel corresponds by performing image analysis of the three-dimensional image data. Then, when a compartment corresponding to the part of the brain in each voxel is specified, the compartment-specifying unit 115 stores the information in the region-of-interest information storage unit 119.

After the process of these steps S101 to S105 is completed, the doctor injects $H_2^{17}O$ into the patient. Then, the doctor measures the time-dependent strength of the nuclear magnetic resonance signal for each voxel in the brain of the patient using the MRI apparatus 120. Here, $^{17}O$ has an effect on H that is bonded thereto.

Accordingly, the strength of the nuclear magnetic resonance signal due to H of $H_2^{17}O$ is different from that of the nuclear magnetic resonance signal due to H of $H_2^{16}O$ present in the brain. On the other hand, $H_2^{17}O$ injected into the patient is diluted by $H_2^{16}O$ in the blood until $H_2^{17}O$ reaches the brain. Therefore, in order to acquire a clear nuclear magnetic resonance signal due to H of $H_2^{17}O$ in the MRI apparatus 120, $H_2^{17}O$ needs to be concentrated to a higher concentration than in natural water. Specifically, it is preferable to use $H_2^{17}O$ concentrated to a concentration of 10% or more. In addition, a voxel as a unit of a region where the MRI apparatus 120 measures the strength of a nuclear magnetic resonance signal is the voxel divided in step S104. For example, the MRI apparatus 120 measures the strength of the nuclear magnetic resonance signal for each voxel in the brain while referring to the voxel position information stored in the region-of-interest information storage unit 119 of the compartmental analyzer 110. Then, the MRI apparatus 120 outputs data, which indicates the strength of the nuclear magnetic resonance signal for each voxel in the brain measured over time, sequentially to the compartmental analyzer 110.

When the data indicating the strength of the nuclear magnetic resonance signal for each voxel in the brain is sequentially acquired from the MRI apparatus 120 (S106), the strength data acquisition unit 116 of the compartmental analyzer 110 stores the information of the strength of the nuclear magnetic resonance signal for each voxel in the brain, which is indicated by the data when $H_2^{17}O$ reaches the brain, in the region-of-interest information storage unit 119. Here, "when $H_2^{17}O$ reaches the brain" may be "when a predetermined time elapses after injecting $H_2^{17}O$" or may be "when the strength of a nuclear magnetic resonance signal in a predetermined part in the brain exceeds a predetermined threshold", for example.

When the information of the strength of the nuclear magnetic resonance signal for each voxel is stored in the region-of-interest information storage unit 119, the rate constant calculation unit 117 of the compartmental analyzer 110 calculates a rate constant when $H_2^{17}O$ moves between compartments on the basis of the strength of the nuclear magnetic resonance signal in the first compartment, the strength of the nuclear magnetic resonance signal in the second compartment, and the strength of the nuclear magnetic resonance signal in the third compartment (S107). Here, the strength of the nuclear magnetic resonance signal may be regarded as the concentration of $H_2^{17}O$ in the part. That is, when $H_2^{17}O$ is present in a certain part, the strength of the nuclear magnetic resonance signal in the part may be regarded as the concentration of $H_2^{17}O$.

In the following explanation, the concentration of $H_2^{17}O$ at a certain time t in the first compartment is set to Bl(t), the concentration of $H_2^{17}O$ at the same time t in the second compartment is set to Br(t), and the concentration of $H_2^{17}O$ at the same time t in the third compartment is set to C(t). In addition, in the following explanation, the rate constant when $H_2^{17}O$ moves from the first compartment to the second compartment is set to K1, the rate constant when $H_2^{17}O$ moves from the second compartment to the first compartment is set to K2, the rate constant when $H_2^{17}O$ moves from the first compartment to the third compartment is set to K3, the rate constant when $H_2^{17}O$ moves from the third compartment to the first compartment is set to K4, the rate constant when $H_2^{17}O$ moves from the third compartment to the second compartment is set to K5, and the rate constant when $H_2^{17}O$ moves from the second compartment to the third compartment is set to K6.

In this case, time variation dBr(t)/dt of Br(t) can be expressed as Expression (1), for example.

[Expression 1]

$$dBr(t)/dt = K1 \cdot Bl(t) + K5 \cdot C(t) - (K2 + K6) \cdot Br(t) \quad (1)$$

In addition, time variation dC(t)/dt of C(t) can be expressed as Expression (2), for example.

[Expression 2]

$$dC(t)/dt = K3 \cdot Bl(t) + K6 \cdot Br(t) - (K5 + K4) \cdot C(t) \quad (2)$$

In addition, time variation dBl(t)/dt of Bl(t) can be expressed as Expression (3), for example.

[Expression 3]

$$dBl(t)/dt = K2 \cdot Br(t) + K4 \cdot C(t) - (K1 + K3) \cdot Bl(t) \quad (3)$$

The rate constant calculation unit 117 applies the value of the strength of the nuclear magnetic resonance signal for each voxel, which is stored in the region-of-interest information storage unit 119, to Bl(t), Br(t), and C(t) in Expressions (1) to (3) and also calculates the rate constants K1 to K6 using normal mathematical techniques, such as the Gauss-Newton method, the conjugate gradient method, the least squares method, the modified Marquardt method, and the simplex method.

Thus, the rate constants K1 and K2 obtained by assuming the relationship with the third compartment corresponding to the cerebral sulcus or cerebral ventricle may be different values from K1 and K2 calculated by the analysis method using the two-compartment model in which only the relationship between the cerebral blood vessel and the brain tissue is assumed. In addition, the rate constants K3 to K6 obtained by assuming the relationship with the third compartment corresponding to the cerebral sulcus or cerebral ventricle are rate constants that could not be obtained by the analysis method using the two-compartment model in which only the relationship between the cerebral blood vessel and the brain tissue is assumed.

As described above, according to the compartmental analysis system 100, rate constants more useful than the rate constants obtained by the analysis using the two-compartment models can be calculated as parameters for analyzing the dynamics of cerebral blood flow in the brain. For example, hemodynamics of blood flow or cerebrospinal fluid in each specific location can be checked. In existing examinations, the spatial resolution is poor (pixels (signal acquisition unit) of 10 (mm)×10 (mm) in the case of SPECT (Single Photon Emission Computed Tomography), and pixels 1 (mm)×1 (mm) (may be smaller) in the case of MRI). Accordingly, it is not possible to acquire a detailed local image of cerebral blood flow. In addition, the flow of cerebrospinal fluid is not taken into consideration at all. In contrast, according to the invention, it is possible to check the detailed local cerebral blood flow and cerebrospinal fluid dynamics more accurately. Accordingly, advanced criteria for determining the treatment to be applied to the patient can be obtained. For example, for a cerebral infarction patient, advanced criteria of whether or not to perform thrombolytic therapy can be obtained. That is, determination regarding whether or not a damaged portion of the brain can be recovered by thrombolytic therapy can be made more clearly than in the existing examination. In addition, since functional information of cerebral blood vessels (cerebral blood flow and cerebrospinal fluid circulation capability) is acquired, this may be used to determine whether or not the cerebral blood vessels can withstand thrombolytic therapy. Moreover, in recent years, it has also been suggested that as a result of dementia, the amount of cerebrospinal fluid circulation decreases. From this point of view, since cerebrospinal fluid circulation can be accurately checked, the invention can contribute not only to diagnosis but also to development of therapeutic agents for increasing the amount of cerebrospinal fluid to the normal level.

In addition, although a radioactive chemical may be used as the "tracer" in this invention instead of $H_2^{17}O$, it is preferable to use $H_2^{17}O$ due to the following reasons. Since existing radiopharmaceuticals have short half-lives (for example, since the half-life of $^{15}O$ is extremely short (several minutes)), efficacy as a diagnostic agent does not last long. For this reason, since existing radiopharmaceuticals are not available, the existing radiopharmaceuticals cannot be applied to emergency patients, such as cerebral infarction. In the case of cerebral infarction, diagnosis and treatment within a few hours from development of the symptoms are most effective. However, existing radiopharmaceuticals have a fateful flaw in that diagnosis in this acute phase cannot be performed. In addition, existing radiopharmaceuticals are radioactive isotopes, and are not intrinsically safe materials. The form of a diagnostic agent is also a disadvantage because it is not a physiological substance but chemicals that the human body does not usually take in, in SPECT agents and the like. In contrast, since $H_2^{17}O$ is water, it is possible to acquire a result that reflects the more precise physiological mechanism. In addition, although the number of facilities where radioactive diagnostic agents can be used is 1,000 or less in Japan, the agent for MRI proposed at this time may be used in at least three times the number of facilities as the radioactive diagnostic facilities. In addition, when a radiopharmaceutical is used as a tracer, a PET (Positron Emission Tomography) apparatus or a SPECT apparatus is used as the "measurement apparatus" in this invention instead of the MRI apparatus 120.

In addition, the "rate constant calculation unit" in this invention may be configured to use the signal strengths of a certain number of voxels for each compartment when calculating the rate constant.

In addition, the "rate constant calculation unit" in this invention may calculate a rate constant when a tracer moves between compartments without using the strength of an electromagnetic wave in a first compartment. In this case, instead of the strength of an electromagnetic wave in the first compartment, the "rate constant calculation unit" in this invention calculates the rate constant when a tracer moves between compartments using a temporal measurement result of the amount of tracer sampled from the patient's arterial blood after the tracer is administered to the patient. Alternatively, the "rate constant calculation unit" in this invention may calculate the rate constant when a tracer moves between compartments using an input function to allow the amount of tracer introduced into cerebral blood vessels to be assumed instead of the strength of an electromagnetic wave in the first compartment.

Figure 5:
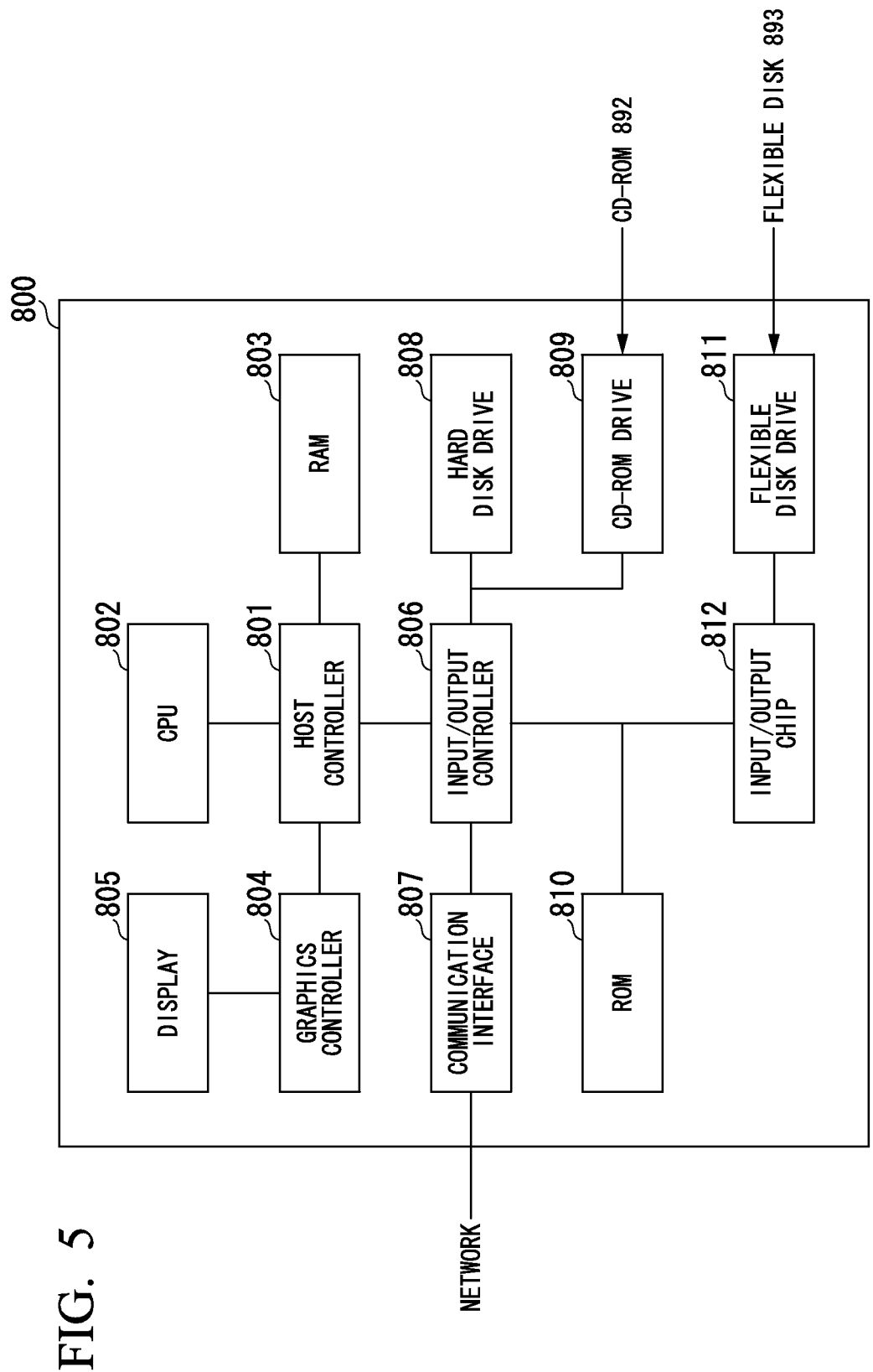
FIG. 5 is a view showing an example of the hardware configuration of a computer 800 that forms the compartmental analyzer 110 according to the present embodiment.

FIG. 5 shows an example of the hardware configuration of a computer 800 that forms the compartmental analyzer 110 according to the present embodiment. The computer 800 according to the present embodiment includes: a CPU periphery having a CPU (Central Processing Unit) 802, a RAM (Random Access Memory) 803, a graphics controller 804, and a display 805 that are connected to each other through a host controller 801; an input/output unit having a communication interface 807, a hard disk drive 808, and a CD-ROM (Compact Disk Read Only Memory) drive 809 that are connected to each other through an input/output controller 806; and a legacy input/output unit having a ROM (Read Only Memory) 810, a flexible disk drive 811, and an input/output chip 812 that are connected to the input/output controller 806.

The host controller 801 connects the RAM 803, the CPU 802, which accesses the RAM 803 at a high transfer rate, and the graphics controller 804 to each other. The CPU 802 operates on the basis of programs stored in the ROM 810 and the RAM 803, and controls each unit. The graphics controller 804 acquires image data, which is generated on a frame buffer provided in the RAM 803 by the CPU 802 or the like, and displays the image data on the display 805. Instead of this, the graphics controller 804 may include a frame buffer that stores the image data generated by the CPU 802 or the like.

The input/output controller 806 connects the host controller 801, the communication interface 807, which is a relatively high-speed input/output device, the hard disk drive 808, and the CD-ROM drive 809 to each other. The hard disk drive 808 stores data and programs used by the CPU 802 in the computer 800. The CD-ROM drive 809 reads a program or data from a CD-ROM 892 and provides it to the hard disk drive 808 through the RAM 803.

In addition, the ROM 810, the flexible disk drive 811, and a relatively low-speed input/output device of the input/output chip 812 are connected to the input/output controller 806. A boot program executed at the start time of the computer 800 and/or a program depending on the hardware of the computer 800 are stored in the ROM 810. The flexible disk drive 811 reads a program or data from a flexible disk 893 and provides it to the hard disk drive 808 through the RAM 803. The input/output chip 812 connects the flexible disk drive 811 to the input/output controller 806 and also connects various kinds of input/output devices to the input/output controller 806 through a parallel port, a serial port, a keyboard port, or a mouse port, for example.

A program provided to the hard disk drive 808 through the RAM 803 is stored on a recording medium, such as the flexible disk 893, the CD-ROM 892, or an IC (Integrated Circuit) card, and is provided by the user. The program is read from the recording medium, is installed in the hard disk drive 808 in the computer 800 through the RAM 803, and is executed in the CPU 802.

The program, which is installed in the computer 800 and causes the computer 800 to function as the compartmental analyzer 110, causes the computer 800 to function as the rate constant calculation unit 117 that calculates a rate constant when $H_2^{17}O$ moves between the compartments on the basis of the strength of the nuclear magnetic resonance signal in the first compartment in the brain measured by the MRI apparatus 120, the strength of the nuclear magnetic resonance signal in the second compartment in the brain measured by the MRI apparatus 120, and the strength of the nuclear magnetic resonance signal in the third compartment in the brain measured by the MRI apparatus 120 in step S107.

In addition, the program may cause the computer 800 to function as the compartment-specifying unit 115 that specifies to which one of the first compartment corresponding to the cerebral blood vessel, the second compartment corresponding to brain tissue, and the third compartment corresponding to the cerebral sulcus or cerebral ventricle a part of the brain in each of the plurality of voxels obtained by dividing the brain corresponds in step 5105 and the rate constant calculation unit 117 that calculates a rate constant when $H_2^{17}O$ moves between the compartments on the basis of the strength of the nuclear magnetic resonance signal in a voxel specified to correspond to the first compartment by the compartment-specifying unit 115, the strength of the nuclear magnetic resonance signal in a voxel specified to correspond to the second compartment by the compartment-specifying unit 115, and the strength of the nuclear magnetic resonance signal in a voxel specified to correspond to the third compartment by the compartment-specifying unit 115 in step S107.

In addition, the program may cause the computer 800 to function as the region division unit 114 that divides a brain into a plurality of voxels in step S104 and the compartment-specifying unit 115 that specifies to which one of the compartments a part of the brain in each of the plurality of voxels divided by the region division unit 114 corresponds in step S105.

In addition, the program may cause the computer 800 to function as the instruction-receiving unit 113 that receives an instruction to specify a region-of-interest of the brain, which is to be subjected to compartmental analysis, through the input device 130 in step S103 and the region division unit 114 that divides the region-of-interest, which is specified by the instruction received by the instruction-receiving unit 113, into a plurality of voxels in step S104.

In addition, the program may cause the computer 800 to function as the image data acquisition unit 111 that acquires three-dimensional image data of the photographed brain from the MRI apparatus 120 in step S101.

In addition, the program may cause the computer 800 to function as the image data output unit 112 that outputs the three-dimensional image data of the photographed brain to the output device 140 in step S102.

In addition, the program may cause the computer 800 to function as the strength data acquisition unit 116 that acquires data, which indicates the strength of a nuclear magnetic resonance signal for each voxel in the brain, from the MRI apparatus 120 in step S106.

The information processing described in these programs is loaded into the computer 800 to function as the image data acquisition unit 111, the image data output unit 112, the instruction-receiving unit 113, the region division unit 114, the compartment-specifying unit 115, the strength data acquisition unit 116, the rate constant calculation unit 117, the image data storage unit 118, and the region-of-interest information storage unit 119 which are specific means of software and various kinds of hardware resources described above that cooperate with each other. In addition, by realizing an operation or processing of the information according to the purpose of use of the computer 800 in the present embodiment using the specific means, the compartmental analyzer 110 specific to the purpose of use is constructed.

As an example, when performing communication between the computer 800 and an external apparatus or the like, the CPU 802 executes a communication program loaded on the RAM 803 and instructs the communication interface 807 to perform communication processing on the basis of the content of processing described in the communication program. By control of the CPU 802, the communication interface 807 reads the transmission data, which is stored in a transmission buffer region or the like set on a storage device such as the RAM 803, the hard disk drive 808, the flexible disk 893, or the CD-ROM 892 and transmits it through the network or writes the received data, which is received through the network, into a receiving buffer region set on a storage device. Thus, data may be transmitted or received to or from the storage device through the communication interface 807 using the direct memory access method. Instead, data may also be transmitted or received by allowing the CPU 802 to read the data from a storage device at the source or through the communication interface 807 and write the data into a storage device at the destination or through the communication interface 807 at the destination.

In addition, the CPU 802 loads all or some necessary files or a database stored on an external storage device, such as the hard disk drive 808, the CD-ROM 892, or the flexible disk 893, into the RAM 803 by direct memory access transfer or the like and performs various kinds of processing on the data in the RAM 803. Then, the CPU 802 writes the data after the processing into the external storage by direct memory access transfer or the like.

In such processing, it can be regarded that the RAM 803 holds the content of an external storage device temporarily. In the present embodiment, therefore, the RAM 803, the external storage device, and the like are collectively called a memory, a storage unit, a storage device, or the like. In the present embodiment, various kinds of information, such as various programs, data, tables, and a database, are stored on such a storage device to become objects of information processing. In addition, the CPU 802 can hold a part of the RAM 803 in a cache memory and perform reading and writing on the cache memory. Also in such a form, the cache memory has a part of the function of the RAM 803. In the present embodiment, therefore, the cache memory shall also be included in the RAM 803, a memory, and/or a storage device except for the case where the cache memory is distinctively described.

In addition, the CPU 802 performs various kinds of processing, which have been specified by the instruction sequence of the program and which include various kinds of operations, processing of information, determination of conditions, information retrieval, and replacement, on the data read from the RAM 803 and writes the result into the RAM 803. For example, in the case of determination of conditions, the CPU 802 determines whether or not various variables shown in the present embodiment satisfy predetermined conditions are greater than other variables or constants, whether or not various variables are smaller than other variables or constants, whether or not various variables are equal to or greater than other variables or constants, whether or not various variables are equal to or less than other variables or constants, or whether or not various variables are equal to other variables or constants. When the conditions are satisfied or not satisfied, the CPU 802 branches to different instruction sequences or calls a subroutine.

In addition, the CPU 802 can retrieve the information stored in files, a database, and the like on the storage device. For example, when a plurality of entries in which the attribute value of a second attribute is matched with the attribute value of a first attribute are stored on the storage device, the CPU 802 can obtain the attribute value of the second attribute matched with the first attribute, which satisfies predetermined conditions, by retrieving an entry matching the conditions, in which the attribute value of the first attribute is specified, from the plurality of entries stored on the storage device and reading the attribute value of the second attribute stored in the entry.

The above-described programs or modules may be stored on the external storage medium. Not only the flexible disk 893 and the CD-ROM 892 but also optical recording media such as a DVD (Digital Versatile Disc) or a CD (Compact Disc), magneto-optical recording media such as an MO (Magneto-Optical disc), tape media, a semiconductor memory such as an IC card, and the like may be used as storage media. In addition, storage media, such as a hard disk, a RAM, and the like, provided in a server system connected to a private communication network or the Internet may be used as recording media, and a program may be provided to the computer 800 through the network.

While the invention has been described using the embodiment, the technical scope of the invention is not limited to the scope described in the embodiment described above. It is apparent to those skilled in the art that various modifications or improvements may be made to the embodiment described above. It is apparent from the appended claims that such modifications or improvements may also be included in the technical scope of the invention.

It should be noted that the order of execution of each process of the operations, procedures, steps, and the like in the system, the method, the apparatus, the program, and the recording medium described in the appended claims, specification, and drawings may be implemented in any order unless "before", "in advance", and the like are particularly expressed and the output of a previous process is used in the next process. For the operation flows in the appended claims, specification, and drawings, even if the operation flows are described using "first", "next", and the like for convenience, it does not mean that the operation flows should be executed in this order.

While preferred embodiments of the invention have been described and illustrated above, it should be understood that these are exemplary of the invention and are not to be considered as limiting. Additions, omissions, substitutions, and other modifications can be made without departing from the spirit or scope of the present invention. Accordingly, the invention is not to be considered as being limited by the foregoing description, and is only limited by the scope of the appended claims.

What is claimed is:

1. A compartmental analysis system that performs compartmental analysis of dynamics of a tracer in a brain, comprising:
a measurement apparatus comprising at least one processor that measures a strength of an electromagnetic wave from the tracer in the brain; and
a compartmental analyzer comprising at least one processor that performs compartmental analysis of dynamics of the tracer in the brain on the basis of the strength of the electromagnetic wave from the tracer in the brain measured by the measurement apparatus,
wherein the compartmental analyzer includes a rate constant calculation unit comprising at least one processor that calculates at least one rate constant when the tracer moves between compartments of a brain on the basis of a strength of an electromagnetic wave in a first compartment corresponding to a cerebral blood vessel in the brain measured by the measurement apparatus or an input function in the first compartment, a strength of an electromagnetic wave in a second compartment corresponding to brain tissue in the brain measured by the measurement apparatus, and a strength of an electromagnetic wave in a third compartment corresponding to a cerebral sulcus or a cerebral ventricle in the brain measured by the measurement apparatus.

2. The compartmental analysis system according to claim 1, wherein the compartmental analyzer further includes a compartment-specifying unit comprising at least one processor that specifies to which one of the compartments a part of the brain in each of a plurality of divided regions obtained by dividing the brain corresponds, and wherein the rate constant calculation unit calculates the at least one rate constant when the tracer moves between the compartments on the basis of a strength of an electromagnetic wave in a divided region specified to correspond to the first compartment by the compartment-specifying unit, a strength of an electromagnetic wave in a divided region specified to correspond to the second compartment by the compartment-specifying unit, and a strength of an electromagnetic wave in a divided region specified to correspond to the third compartment by the compartment-specifying unit.

3. The compartmental analysis system according to claim 2, wherein the compartmental analyzer further includes a region division unit comprising at least one processor that divides the brain into a plurality of divided regions, and wherein the compartment-specifying unit specifies to which one of the compartments a part of the brain in each of the plurality of divided regions divided by the region division unit corresponds.

4. The compartmental analysis system according to claim 3, wherein the compartmental analyzer further includes an instruction-receiving unit comprising at least one processor that receives an instruction to specify a region-of-interest of the brain, which is to be subjected to compartmental analysis, and wherein the region division unit divides the region-of-interest, which is specified by the instruction received by the instruction-receiving unit, into a plurality of divided regions.

5. The compartmental analysis system according to claim 1, wherein the tracer is $H_2^{17}O$.

6. The compartmental analysis system according to claim 5, wherein the measurement apparatus is an MRI apparatus.

7. The compartmental analysis system according to claim 1, wherein the measurement apparatus is an MRI apparatus.

8. The compartmental analysis system according to claim 1, wherein the rate constant calculation unit calculates a plurality of rate constants.

9. The compartmental analysis system according to claim 8, wherein the rate constant calculation unit calculates a first rate constant that is representative of how the tracer moves between a first compartment corresponding to a cerebral blood vessel in the brain and a second compartment corresponding to brain tissue in the brain, and a second rate constant that is representative of how the tracer moves between the second compartment corresponding to brain tissue in the brain and a third compartment corresponding to a cerebral sulcus or a cerebral ventricle in the brain.

10. A compartmental analysis method of performing compartmental analysis of dynamics of a tracer in a brain on the basis of a strength of an electromagnetic wave from the tracer in the brain measured by a measurement apparatus, wherein the method comprises:

measuring, with a measurement apparatus, a strength of an electromagnetic wave of a tracer in at least one compartment of a brain; and calculating at least one rate constant when the tracer moves between compartments of a brain on the basis of the measured strength of the electromagnetic wave in a first compartment corresponding to a cerebral blood vessel in the brain measured by the measurement apparatus or an input function in the first compartment, a strength of an electromagnetic wave in a second compartment corresponding to brain tissue in the brain measured by the measurement apparatus, and a strength of an electromagnetic wave in a third compartment corresponding to a cerebral sulcus or a cerebral ventricle in the brain measured by the measurement apparatus.

11. The compartmental analysis method of claim 10, wherein the calculating step comprises calculating a plurality of rate constants.

12. The compartmental analysis method of claim 11, wherein the calculating step comprises:

calculating a first rate constant that is representative of how the tracer moves between a first compartment corresponding to a cerebral blood vessel in the brain and a second compartment corresponding to brain tissue in the brain; and calculating a second rate constant that is representative of how the tracer moves between the second compartment corresponding to brain tissue in the brain and a third compartment corresponding to a cerebral sulcus or a cerebral ventricle in the brain.

13. A compartmental analyzer that performs compartmental analysis of dynamics of a tracer in a brain on the basis of a strength of an electromagnetic wave from the tracer in the brain measured by a measurement apparatus, wherein the compartmental analyzer comprising:

a rate constant calculation unit comprising at least one processor that calculates at least one rate constant when the tracer moves between compartments of a brain on the basis of a strength of an electromagnetic wave in a first compartment corresponding to a cerebral blood vessel in the brain measured by the measurement apparatus or an input function in the first compartment, a strength of an electromagnetic wave in a second compartment corresponding to brain tissue in the brain measured by the measurement apparatus, and a strength of an electromagnetic wave in a third compartment corresponding to a cerebral sulcus or a cerebral ventricle in the brain measured by the measurement apparatus.

14. The compartmental analyzer according to claim 13, wherein the rate constant calculation unit calculates a plurality of rate constants.

15. The compartmental analyzer according to claim 14, wherein the rate constant calculation unit calculates a first rate constant that is representative of how the tracer moves between a first compartment corresponding to a cerebral blood vessel in the brain and a second compartment corresponding to brain tissue in the brain, and a second rate constant that is representative of how the tracer moves between the second compartment corresponding to brain tissue in the brain and a third compartment corresponding to a cerebral sulcus or a cerebral ventricle in the brain.

16. A non-transitory computer readable medium storing a program which, when run by one or more processors, causes the one or more processors to perform compartmental analysis of dynamics of a tracer in a brain on the basis of a strength of an electromagnetic wave from the tracer in the brain measured by a measurement apparatus, wherein the program causes the one or more processors to function as:

a rate constant calculation unit that calculates at least one rate constant when the tracer moves between compartments of a brain on the basis of a strength of an electromagnetic wave in a first compartment corresponding to a cerebral blood vessel in the brain measured by the measurement apparatus or an input function in the first compartment, a strength of an electromagnetic wave in a second compartment corresponding to brain tissue in the brain measured by the measurement apparatus, and a strength of an electromagnetic wave in a third compartment corresponding to a cerebral sulcus or a cerebral ventricle in the brain measured by the measurement apparatus.

17. The non-transitory computer readable medium of claim 16, wherein the program causes the one or more processors to function as a rate constant calculation unit that calculates a plurality of rate constants.

18. The non-transitory computer readable medium of claim 17, wherein the program causes the one or more processors to function as a rate constant calculation unit that calculates a first rate constant that is representative of how the tracer moves between a first compartment corresponding to a cerebral blood vessel in the brain and a second compartment corresponding to brain tissue in the brain, and a second rate constant that is representative of how the tracer moves between the second compartment corresponding to brain tissue in the brain and a third compartment corresponding to a cerebral sulcus or a cerebral ventricle in the brain.

* * * * *